(12) United States Patent
Castelli et al.

(10) Patent No.: US 10,588,538 B2
(45) Date of Patent: Mar. 17, 2020

(54) MEDICAL IMAGING SYSTEM HAVING MICROWAVE EMISSION/RECEPTION

(71) Applicants: MVG INDUSTRIES, Villebon sur Yvette (FR); OFFICE NATIONAL D'ETUDES ET RECHERCHES AEROSPATIALES (ONERA), Chatillon (FR)

(72) Inventors: Juan Carlos Castelli, Chatillon (FR); Luc Duchesne, Angervilliers (FR); Virginie Tessier, Le Plessis Robinson (FR); Ludovic Durand, Marcoussis (FR); Philippe Garreau, Paris (FR); Nicolas Adnet, Villebon sur Yvette (FR); Stéphane Thiébaut, Villebon sur Yvette (FR)

(73) Assignees: MVG INDUSTRIES, Villebon sur Yvette (FR); OFFICE NATIONAL D'ETUDES ET RECHERCHES AEROSPATIALES (ONERA), Chatillon (FR)

( * ) Notice: Subject to any disclaimer, the term of this patent is extended or adjusted under 35 U.S.C. 154(b) by 293 days.

(21) Appl. No.: 14/895,903

(22) PCT Filed: Jun. 6, 2014

(86) PCT No.: PCT/EP2014/061913
§ 371 (c)(1),
(2) Date: Dec. 3, 2015

(87) PCT Pub. No.: WO2014/195502
PCT Pub. Date: Dec. 11, 2014

(65) Prior Publication Data
US 2016/0120439 A1    May 5, 2016

(30) Foreign Application Priority Data
Jun. 6, 2013 (FR) .................................. 13 55225

(51) Int. Cl.
*A61B 5/00* (2006.01)
*A61B 5/05* (2006.01)
*G01S 13/89* (2006.01)

(52) U.S. Cl.
CPC .......... *A61B 5/0507* (2013.01); *A61B 5/4312* (2013.01); *A61B 5/708* (2013.01);
(Continued)

(58) Field of Classification Search
CPC ........................... A61B 5/0507; A61B 5/0536
See application file for complete search history.

(56) References Cited

U.S. PATENT DOCUMENTS 4,641,659 A * 2/1987 Sepponen ................ A61B 5/05
600/430
5,829,437 A * 11/1998 Bridges .................... A61B 5/05
324/638
(Continued)

FOREIGN PATENT DOCUMENTS

WO    2005078462 A1    8/2005
WO    WO 2012048020 A1 *  4/2012    ........... A61B 5/0507
(Continued)

OTHER PUBLICATIONS

Rapport De Recherche Preliminaire, Republic Francaise, Institut National De La Propriete Industrielle, Feb. 7, 2014.
(Continued)

*Primary Examiner* — Joseph M Santos Rodriguez
(74) *Attorney, Agent, or Firm* — Park, Vaughan, Fleming & Dowler LLP; Shane Nelson (57) ABSTRACT

The invention relates to a medical imaging system having microwave emitting antennas and antennas for receiving the electromagnetic field, which are arranged around a space for receiving a human tissue medium to be observed, and comprising: an array (3) of emitting antennas and an array
(Continued)

(4) of receiving antennas, wherein said two arrays (3, 4) are independent, and motors capable of angularly rotating and of translating the emitting array (3) and/or the receiving array (4) relative to the space under observation, in order to enable the scanning thereof.

17 Claims, 4 Drawing Sheets (52) U.S. Cl.
CPC .. *A61B 2562/0228* (2013.01); *A61B 2562/143* (2013.01); *G01S 13/89* (2013.01)

(56) References Cited

U.S. PATENT DOCUMENTS

| | | | |
|---|---|---|---|
| 2004/0077943 A1 | 4/2004 | Meaney et al. | |
| 2005/0107692 A1 | 5/2005 | Li et al. | |
| 2006/0241409 A1 | 10/2006 | Winters et al. | |
| 2010/0113921 A1* | 5/2010 | Fear | A61B 5/0062 600/430 |
| 2011/0166445 A1* | 7/2011 | Leibfritz | A61B 5/0507 600/425 |
| 2013/0018591 A1 | 1/2013 | Grzegorczyk | |
| 2013/0116572 A1 | 5/2013 | Son et al. | |
| 2013/0225988 A1* | 8/2013 | Mahfouz | A61B 5/0507 600/430 |

FOREIGN PATENT DOCUMENTS

| | | |
|---|---|---|
| WO | 2004045181 A1 | 3/2014 |
| WO | 2014045181 A1 | 3/2014 |

OTHER PUBLICATIONS

Rapport De Recherche Internationale, PCT/EP2014/061913, Authorized Official, Albrecht, Ronald, effective date of the report Jun. 30, 2014.

Fear, E.C. et al. : Microwave System for Breast Tumor Detection, IEEE Microwave and Guided Wave Letters, IEEE Inc, New York, US, vol. 9. No. 11, Nov. 1, 1999, XP011035499, ISSN: 1051-8207.

Chao, Liu et al.: A Millimeter Wave Breast Cancer Imaging Methodology, Precision Electromagnetic Measurements, (CPEM), 2012 Conference on IEEE, Jul. 1, 2012 (Jul. 1, 2012), pp. 74-75, XP032210932, DOI: 10.1109/CPEM.2012.6250667, ISBN 978-1-4673-0439-9.

Klemm, Maciej et al.: Microwave Radar-Based Differential Breast Cancer Imaging in Homogeneous Breast Phantoms and Low Contrast Scenarios, IEEE transactions on Antennas and Propagation, IEEE Service Center, Piscataway, NJ, US vol. 58, No. 7, Jul. 1, 2010 (Jul. 1, 2010), pp. 2337-2344, XP011307911, ISSN: 0018-926X.

Amineh, R. K., et al.: Ultra-Wide band TEM Horn Antenna for Microwave Imaging of the Breast, Antennas and Propagation Society International Symposium, 2009, APSURSI '09, IEEE, Piscataway, NJ, USA, Jun. 1, 2009, (Jun. 1, 2009), pp. 1-4, XP031536039, ISBN: 978-1-4244-3647-7.

PCT/EP2014/061913 International Search Report dated Jun. 30, 2014.

Maciej Klemm et al: "Microwave Radar-Based Differential Breast Cancer Imaging: Imaging in Homogeneous Breast Phantoms and Low Contrast Scenarios", IEEE Transactions on Antennas and Propagation, IEEE Service Center, Piscataway, NJ, US, vol. 58, No. 7, Jul. 1, 2010 (Jul. 1, 2010), pp. 2337-2344, XP011307911, ISSN: 0018-926X.

Amineh R K et al: "Ultra-wide band TEM horn antenna for microwave imaging of the breast", Antennas and Propagation Society International Symposium, 2009. APSURSI '09. IEEE, IEEE, Piscataway, NJ, USA, Jun. 1, 2009 (Jun. 1, 2009), pp. 1-4, XP031536039, ISBN: 978-1-4244-3647-7.

Fear E C et al: "Microwave System for Breast Tumor Detection", IEEE Microwave and Guided Wave Letters, IEEE Inc, New York, US, vol. 9, No. 11, Nov. 1, 1999 (Nov. 1, 1999), XP011035499, ISSN: 1051-8207 alinea "Proposed System and Modeling".

Liu Chao et al: "A millimeter wave breast cancer imaging methodology", X,P Precision Electromagnetic Measurements (CPEM), 2012 Conference on, IEEE, Jul. 1, 2012 (Jul. 1, 2012), pp. 74-75, XP032210932, DOI: 10.1109/CPEM.2012.6250667 ISBN: 978-1-4673-0439-9 alineas "Measurement Technique" et "Experimental Result".

* cited by examiner

MEDICAL IMAGING SYSTEM HAVING MICROWAVE EMISSION/RECEPTION

GENERAL FIELD AND PRIOR ART

The present invention relates to a medical imaging system with microwave antennas.

More particularly, the invention relates to imaging systems of this type for analysis of human tissue or organs permeable to electromagnetic waves.

It applies in particular and advantageously to imaging of the breast.

In microwave imaging systems, the choice of transition material between the antennas and the medium under observation is important to ensure proper penetration of waves into this medium. The dielectric characteristics of the transition material must be selected as a function of the medium to be observed to obtain better results at the level of the images.

Also, ideally this transition material must have the fewest dielectric losses possible to limit the absorption of energy of the electromagnetic wave.

For this purpose it is ensured most often to immerse the antennas in a liquid with the biological tissues to be imaged. However, even if it is possible to modify the nature of the liquid to obtain the preferred dielectric permittivity such liquid generally has many dielectric losses at preferred working frequencies.

It also poses difficulties in terms of sealing, insulation of the transmitter/sensor probes with the medium under observation, hygiene, cleaning, conservation over time, variation in electromagnetic characteristics over time and as a function of temperature.

Microwave imaging systems employing mixed transition media, comprising a transition medium and a solid transition medium have also been proposed.

By way of example, the article Microwave radar-based differential breast cancer imaging: imaging in homogeneous breast phantoms and low-contrast scenarios—Klemm et al., IEEE—2010 proposes a microwave imaging system using a solid transition medium consisting of a container made of ceramic material in which are positioned adjusting shells adapted to the different sizes of breast and antennas mechanically supported by an envelope made of plastic material which is attached to said container with a transition medium between the envelope made of plastic material and the container made of ceramic material, this transition medium located between the antennas and the container.

Such a system however raises a certain number of difficulties.

The emission/reception structure proposed in the article mentioned hereinabove is limited in terms of robustness of imaging results obtained given the low number of fixed antennas distributed around the shell.

Also, the use of an envelope made of plastic material on the one side and a shell made of ceramic on the other is a source of echoes for signals at the level of transition between the two materials. The measurements are therefore potentially perturbed.

Likewise, due to their close proximity the transmission and reception antennas are not properly electromagnetically insulated from each other. Between them there is an electromagnetic coupling which is all the more significant since the probes are close. But the signal received by the reception probe and due to direct coupling with a transmitting probe is generally strong and limits the dynamics of the receiver. To reconstruct the image of the medium observed it is necessary to proceed to subtraction processing of the signals. The errors engendered by these subtractions are all the more substantial since direct coupling is itself important.

Further still, the structure described in this article is necessarily complex and costly cabling, requiring particularly complicated switching matrices (and associated connections) between probes. This structure needs either switches to select the transmission probe and the reception probe, or multiple transmitters and receivers or the combination of both.

PRESENTATION OF THE INVENTION

The invention proposes as such a solution which eliminates the disadvantages of the prior art.

Especially, it proposes a medical imaging system with transmission antennas and reception antennas of the electromagnetic field arranged around a volume intended to receive human tissue medium to be observed.

It comprises an array of transmission antennas and an array of reception antennas, these two arrays being independent (and especially mechanically independent). Motorisations are provided which are adapted to move the transmission array and or the reception array in angular rotation and in translation relative to the volume under observation to enable scanning of the latter. The system is capable of operating in total multi-state in terms of imaging.

According to a possible aspect, the two arrays are independent in rotation and in translation.

In particular as for translation, this enables oversampling along displacement in translation. Advantageously, the system comprises a shell made of solid dielectric material defining the volume intended to receive human tissue medium to be observed, the transmission antennas and the reception antennas being maintained in array in supports based on dielectric material of dielectric permittivity identical to that of said shell.

Said supports preferably comprise parts made of electromagnetically absorbent material between the antennas or said supports entirely consist of electromagnetically absorbent material. This electromagnetically absorbent material also has dielectric permittivity identical to that of the shell.

The system advantageously also comprises electronics which perform differentiation at least of the reception antennas by modulation.

The invention also relates to a medical imaging process of human tissue medium to be observed comprising the step consisting of moving at least one of the transmission and/or reception arrays relative to the volume under observation to enable scanning of the latter, the microwaves sent by the transmission array, and arriving at a shell intended to receive the human tissue medium, passing through an only solid transition medium.

PRESENTATION OF FIGURES

Other characteristics, aims and advantages of the present invention will emerge from the following detailed description by way of the appended figures given by way of non-limiting examples, and in which.

DESCRIPTION OF ONE OR MORE EMBODIMENTS

Figure 1:
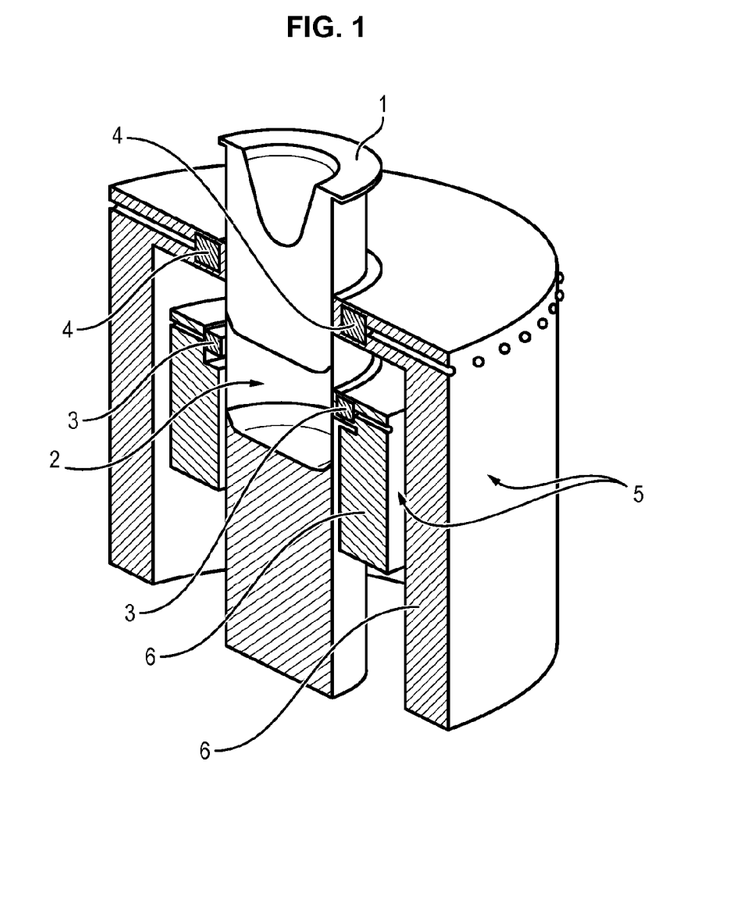
FIG. 1 is a schematic representation in semi-perspective illustrating a possible embodiment for the invention.

In the embodiment of FIG. 1, the device comprises a shell made of dielectric material 1 intended to receive the breast of the patient, a container 2 in which is placed this shell 1, at least one array 3 of transmission probes 3a, at least one array 4 of reception probes 4a, and a set of metallic casings 5 and electromagnetic absorbents 6 made of foam which enclose the container 2 and the arrays 3 and 4.

The shell 1 has an external form complementary to the internal form, cylindrical in this case, of the container 2 in which it is kept. Inside it has a hollow impression intended to receive the breast of a patient.

This shell 1 is detachable relative to the container 2. The device is connected to a set of shells 1. The external forms of the shells of the set of shells are identical. But the impressions are different and allow adaptation to the size of the breasts to be imaged.

Figure 3:
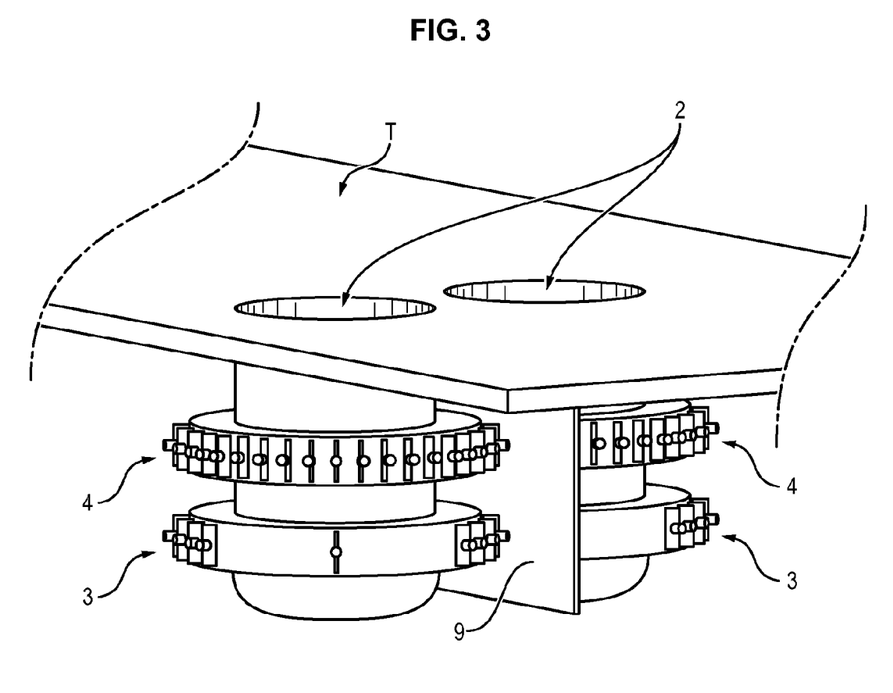
FIG. 3 illustrates yet another possible embodiment for the invention.
Figure 4:
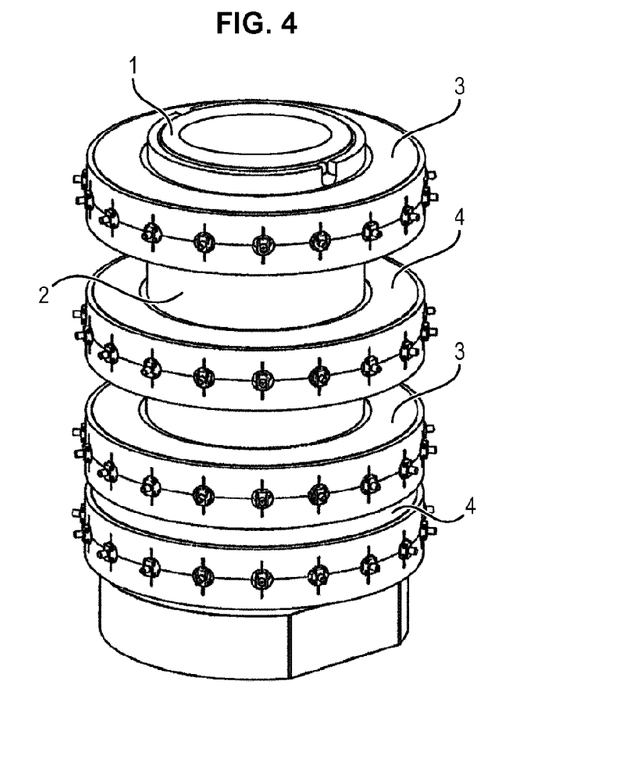
FIG. 4 illustrates yet another possible embodiment for the invention with several transmission and/or reception arrays.

The array 3 of transmission antennas 3a illuminates the medium under observation. In this case, the antennas 3a which compose it can be distributed uniformly, preferably in one plane so as to at least partially enclose the container 2 (FIG. 2), or even according to a ring which encloses the container 2 (FIGS. 1, 3 and 4). The reception array 4 is as such also an array of antennas 4a distributed uniformly, preferably in one plane, so as to at least partially enclose the container 2 (FIG. 2), or even according to a ring which entirely encloses the container 2 (FIGS. 1, 3 and 4).

The array 3 of transmission antennas 3a and the array 4 of reception antennas 4a are both mobile in translation along the container 2. Also, the reception array 4 is mobile in rotation according to angular movement around the container 2 and the medium to be imaged, especially around an axis colinear to translation and preferably in its plane, which when required performs reception oversampling. The array 3 can also be mobile in rotation around the container 2, especially around the same axis colinear to translation as the reception array 4 and preferably in its plane. Motorisations (not shown) are provided to allow the preferred different rotation/translation movements.

As will be evident, the transmission array 3 and the reception array 4 are independent in their movements and positioning around the shell 2, which enables a wide possible choice of transmission and reception combinations and therefore complete multistatic processing and better imaging performance, and enables a number of antennas and limited complexity and cabling costs. In particular, and as illustrated, the transmission array 3 and the reception array 4 can be mechanically independent both in their movement of angular rotation and in their translation movement.

Several transmission arrays 3 and/or several reception arrays 4 can be provided (see FIG. 4). This enables a wider possible choice of combinations of transmission and of reception. For example, in the case of two transmission arrays 3 and two reception arrays 4 these can be stacked on each other so that the transmission arrays 3 alternate with the reception arrays 4, or the transmission arrays 3 are located on either side of the reception arrays 4 and vice versa.

Each transmission array 3, in addition to being mechanically independent of the reception arrays 4, can be mechanically independent on the other transmission arrays 3. Similarly, each reception array 4, in addition to being mechanically uncoupled from the transmission arrays 3, can be mechanically independent of the other reception arrays 4. Yet, it is possible to make the transmission arrays 3 mechanically dependent on each other and the reception arrays 4 mechanically dependent on each other.

In the case of a plurality of transmission arrays 3, and/or reception arrays 4, the transmission 3 and reception 4 arrays can be superposed and the translation path of each of the arrays is limited by the adjacent arrays. This further reduces the translation paths of the different arrays and reduces the overall duration of complete acquisition around the container. For example, each of the arrays 3, 4 is mobile in translation between a first and second end position: when two arrays touch, one is in its first end position and the other in its second end position. In this way, each of the arrays is mobile in translation over a course whereof the length is decreased relative to the size of the container 2.

The transmission array(s) 3 and the reception array(s) 4 can be bivalent. That is, they can be configured so as to act as much in transmission mode as in reception mode. A command is provided for the configuration of the arrays in transmission mode, respectively in reception mode. The command is selected so as to compel the configuration of the arrays such that at least one array operates in transmission mode and at least one array operates in reception mode.

The number of antennas 3a of the transmission array 3 is selected as a function of the preferred number of points of illumination. For each point of illumination, the signal is captured successively by all the reception probes, at each point of the "scan" grating, that is, scanning, combining mechanical displacement of the reception array (vertical translation and rotation) and electronic scanning of the reception probes. The multistatic character of the trajectory of the waves can be exploited and the quality of contrast and resolution of the reconstructed images can be heightened.

The antennas 3a of the transmission array 3 are bipolarized antennas for example, while the antennas 4a of the reception array 4 are mono-polarized or bipolarized antennas. In the event where the transmission 3 and reception 4 arrays are bivalent, the antennas 3a, 4a of these arrays are for example identical mono-polarized or bipolarized.

The antennas are also advantageously broadband so as to allow transmission and reception of radiofrequency signals over a wide frequency band, which boosts resolution and contrast of the reconstructed image. For example, the transmission/reception frequencies of the antennas are between 0.5 and 10 GHz.

The device can also comprise absorbent elements arranged between two successive antennas, which electromagnetically insulate the antennas from each other.

An electronic system enables command of displacements of the arrays 3 and 4 (control of motorisations to perform mechanical scanning), management of the mechanical sensors of movement stop or presence sensors of the breast to be analysed, the multiplexing of the probes 3a, 4a and the processing of the radiofrequency signal.

For an example of processing and analysis of reception signals for obtaining 2D or 3D tomographic images, reference could be made for example to the following publications:

Y. Xie, B. Guo, L. Xu, J. Li, and P. Stoica, *"Multistatic adaptative microwave imaging for early breast cancer detection"*, IEEE Trans. Biomed. Eng., vol 53, no. 8, pp 1647-1657, August 2006; and R. Nilavalan, A. Gbedemah, I. J. Craddock, X. Li and S. C. Hagness, *Numerical investigation of breast tumour detection using multi-static radar*, ELECTRONICS LETTERS vol 39, no. 25, December 2003.

The antennas 3a of the array 3, as for those of the array 4, are directly moulded or inserted in material of dielectric permittivity identical to that of the shell. This material supporting the probes preferably has electromagnetically absorbent properties to reduce the couplings between the probes. In this case, in the event of application to imaging systems of the breast, the material in which the antennas are moulded or inserted is in a ring. Other forms of arrays are possible, of course: linear arrays or in open arcs of a circle, for example for imaging systems of the thyroid or knee.

The container 2 also comprises material of dielectric permittivity identical to that of the shell 1. In another embodiment this material constituting the container can have electromagnetically absorbent properties.

The material of the shell 1 and of the container 2 is dielectric material with low losses, for example Eccostock Hik500F of the company Emerson & Cuming.

In its interior, the shell 1 itself is covered by biocompatible material such as Nuflon (TGBBT).

The material constituting the annular supports of the probes of the arrays 3 and 4 is material having both the same dielectric permittivity as that of Eccostock Hik500F and an absorption capacity of electromagnetic waves.

Figure 2:
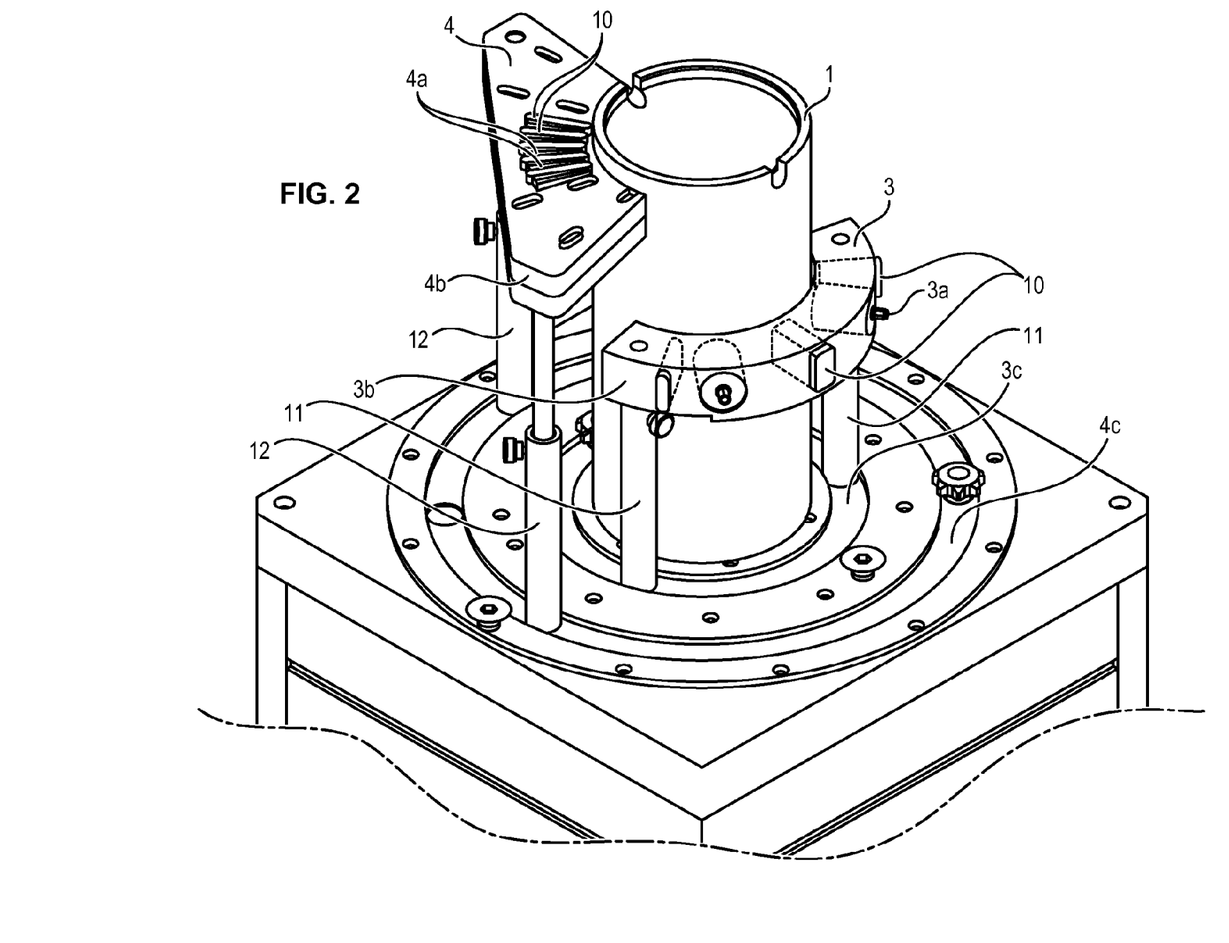
FIG. 2 is a schematic representation in perspective of a ring of transmission antennas and a ring of reception antennas of the device illustrated in FIG. 1.

In another realisation illustrated in FIG. 2, the supports—referenced by 3b and 4b—of the probes of the arrays 3 and 4 can comprise rings made of dielectric material with low losses, for example Eccostock Hik500F, containing inserts 10 between the probes made of material having both the same dielectric permittivity as that of Eccostock Hik500F and an absorption capacity of electromagnetic waves. The support 3b which bears the transmission probes 3a is mounted on jacks 11 which enable shift in translation of said support 3b. These jacks 11 are mounted on an annular rail 3c which allows the support 3b to turn around the axis of the shell 1. The support 4b which bears the reception probes 4a is mounted on jacks 12 which enable shifting in translation of said support 4b. These jacks 12 are mounted on an annular rail 4c which lets the support 4b turn around the axis of the shell 1.

The absorbent solid material is for example based on silicone or epoxy having the same real dielectric permittivity as the material constituting the shell 1. This material is also charged with absorbent powder, for example ferromagnetic fillers, so as to limit direct coupling between the antennas. Such absorbent material enables attenuation of the electromagnetic field of around 4 dB/cm to 1 GHz, 12 dB/cm to 3 GHz, 18 dB/cm to 6 GHz and 18.5 dB/cm to 8 GHz. It is clear that such a solution has the advantage of producing for the device a totally integrated assembly without absorbent foam element which would necessarily be interposed between the probes and which, from the point of view of hygiene (presence of flying particles of carbon), would pose substantial problems.

Also, the fact of using materials of the same dielectric constants for the shell 1, the container 2 and the supports of the antennas of the arrays 3 and 4 avoids the appearance of parasite echoes produced by reflection on the interfaces. Also, the fact that the transmission antennas are rigidly linked together in the same support prevents relative movements and allows excellent adherence to stability of the phases of the signals measured and therefore improved imaging results.

Also, to complete insulation of the probes from each other, it is also possible to provide radiofrequency switches having high insulation characteristics.

Marking on receipt of the probes is also provided, and when required on transmission of the probes, by modulation as per the technique of modulated diffusion which locally marks the field at the point of reception, and when required transmission.

This reduces the complexity and costs of the electronics by dispensing with switch matrices between complex and costly probes. When the transmission and reception antennas are bipolarized, the control electronics (not shown) select the polarization of the working antennas (either by means of switches, or by modulation, or even by combining both).

The metallic casings 5 form partial Faraday cages.

They are associated with absorbent materials, for example supple or rigid foam 6 arranged:
between the two metallic casings 5 and in particular on the inner face of the outer casing 5, on the one hand;
between the arrays 3 and 4 of antennas and said casings, on the other hand.

These materials strongly attenuate, or even eliminate, the echoes of the electromagnetic signal and prevent any artefact of image reconstruction which would be due to multiple reflections.

As illustrated in FIG. 3 for another embodiment, the imaging system can also comprise two juxtaposed containers 2, each associated with a sub-system of transmission/reception arrays 3 and 4.

A metallic plate 9 covered in absorbent material electromagnetically insulating the two containers is interposed between the two sub-systems.

In this way, this decreases by a factor of two the duration of the examination and the evolution of the image obtained and reconstructed is presented simultaneously and in parallel, which allows examination and diagnosis by comparison of both breasts.

Also, as a function of the zones of the medium under observation to be imaged, it can be interesting to incline the transmission and reception system, relative to the plane of the table T on which the patient is positioned, for example an inclination mechanism can be provided to control the inclination of the planes of the arrays symmetrically relative to the metallic plate 9 and so that the antennas 3a, 4a of the arrays closest to the metallic plate 9 move away from the patient, that is, from the plane of the table T, and the antennas 3a, 4a of the arrays farthest from the metallic plate 9 move towards the patient, that is, to the plane of the table T. The angle of inclination of the arrays relative to the plane T of the table is for example of the order of 15 degrees.

In the case of imaging of the breast, this inclination of the planes of the arrays can be useful for scanning the external zones of the breast, and in particular the axillary extension zone of the mammary gland.

In an embodiment, the medical imaging system comprises:
an array 3 of transmission antennas 3a and an array 4 of reception antennas 4a, and
a container 2 configured to receive a shell 1 intended to receive the human tissue medium.

A medical imaging process of human tissue medium, such as for example the breast of a patient, consists of shifting at least one of these arrays relative to the volume under observation receiving the human tissue medium, especially in angular rotation and/or in translation, as mentioned previously. It is possible to shift the arrays 3, 4 in angular rotation and in translation independently of each other.

In a possible embodiment, the microwaves sent by the transmission array and arriving at the shell 1 pass through an only solid transition medium. This only solid transition medium is constituted for example by the container 2 (as in FIG. 1), or by the support 3b and the container 2 (as in FIG. 2). This dispenses with the disadvantages of transition liquid media.

It is noted according to the applications that it is not however obligatory to use an only solid transition medium.

In a particular example, the microwaves sent by the transmission array 3 and arriving at the human tissue medium to be observed (such as the breast of the patient) pass through an only solid transition medium.

This only solid transition medium is constituted for example by the container 2 and the shell 1 (as in FIG. 1), or by the support 3b, the container 2 and the shell 1 (as in FIG. 2).

Therefore, in this non-limiting example, no transition medium is used between the transmission array 3 and the human tissue medium to be observed.

The invention applies especially to imaging of the breast.

The invention claimed is:

1. A medical imaging system with microwave transmission antennas and antennas of reception of the electromagnetic field arranged around a volume intended to receive human tissue medium to be observed, characterized in that it comprises:
a shell (1) defining the volume intended to receive human tissue medium to be observed, the shell (1) having an external form, the external form of the shell (1) being symmetrical in rotation around a vertical axis, the shell (1) being made of solid dielectric material;
an array (3) of transmission antennas (3a) and an array (4) of reception antennas (4a) for microwave imaging, these two arrays (3, 4) being independent, the antennas (3a) of transmission and the antennas (4a) of reception directly coupled to supports (3b, 4b), wherein each of the supports comprise material of dielectric permittivity identical to that of said shell (1); and
one or more motors capable of shifting at least one of the transmission array (3) and the reception array (4) relative to the shell (1) in angular rotation around the vertical axis and in translation along the vertical axis to enable scanning of the volume under observation, the two arrays (3, 4) being independent in rotation and translation, the rotation and the translation of each array being independent.

2. The system according to claim 1, characterized in that said supports (3b, 4b) comprise parts made of electromagnetically absorbent materials between the antennas (3a, 4a).

3. The system according to claim 1, characterized in that the supports (3b, 4b) consist of entirely electromagnetically absorbent material.

4. The system according to claim 2, characterized in that said electromagnetically absorbent material further has dielectric permittivity identical to that of the shell (1).

5. The system according to claim 2, characterized in that the shell (1) is arranged in a container (2) made of dielectric material which the arrays (3, 4) enclose at least partially, the materials of the container (2), the shell (1) and the supports (3b, 4b) of arrays being identical.

6. The system according to claim 5, characterized in that the container (2) is externally cylindrical, at least one of the transmission array (3) and the reception array (4) moving in at least one of translation and rotation about the latter.

7. The system according to claim 1, characterized in that it comprises at least two containers (2).

8. The system according to claim 3, characterized in that the shell (1) is detachable, the system being connected to a set of shells of different internal dimensions.

9. The system according to claim 1, characterized in that it comprises at least one of two arrays (3) of reception antennas (3a) and at least two arrays (4) of transmission antennas (4a).

10. The system according to claim 9, characterized in that each of the arrays (3, 4) of antennas is mobile in translation in a limited way.

11. The system according to claim 1, characterized in that the array(s) (3) of reception antennas (3a) and the array(s) (4) of transmission antennas (4a) are bivalent, the arrays (3, 4) being capable to be configured to operate in transmission mode, respectively in reception mode, the configuration of the arrays (3, 4) being such that at least one array operates in transmission mode and at least one array operates in reception mode.

12. A process for medical imaging of a human tissue medium to be observed, in a medical imaging system with microwave transmission antennas and reception antennas of the electromagnetic field arranged around a volume receiving said human tissue medium, said system comprising:
an array (3) of transmission antennas (3a) and an array (4) of reception antennas (4a) for microwave imaging, and
a container (2) configured to receive a shell (1) intended to receive the human tissue medium, the shell (1) having an external form, the external form of the shell (1) being symmetrical in rotation around a vertical axis, the shell (1) being made of solid dielectric material, the antennas (3a) of transmission and the antennas (4a) of reception directly coupled to supports (3b, 4b), wherein each of the supports comprise material of dielectric permittivity identical to that of said shell (1),
the process comprising the step consisting of shifting at least one of these arrays (3, 4) relative to the shell (1) in at least one of angular rotation around the vertical axis and translation along the vertical axis to enable scanning of the volume under observation, the rotation being independent from the translation, the microwaves sent by the transmission array (3) and arriving at the shell (1) passing through an only solid transition medium.

13. A medical imaging system, comprising:
a shell defining a volume intended to receive human tissue medium to be observed, wherein the shell comprises an external form that is symmetrical in rotation around a vertical axis, wherein the shell comprises a solid dielectric material;
a transmission antenna array directly coupled to a first support;
a reception antenna array directly coupled to a second support; and
one or more motors configured to shift at least one of the transmission antenna array and the reception antenna array relative to the shell in angular rotation around the vertical axis and in translation along the vertical axis,
wherein the first support and the second support each comprise a material of dielectric permittivity identical to the shell.

14. The system according to claim 13,
wherein the transmission antenna array is independent in rotation and translation to the reception antenna array,
wherein each of the transmission antenna array and the reception antenna array is configured to rotate and translate independently.

15. A medical imaging system, comprising:
a shell defining a volume intended to receive human tissue medium to be observed, wherein the shell comprises an external form that is symmetrical in rotation around a vertical axis;
a transmission antenna array directly coupled to a first support;
a reception antenna array directly coupled to a second support; and
one or more motors configured to shift at least one of the transmission antenna array and the reception antenna array relative to the shell in angular rotation around the vertical axis and in translation along the vertical axis,
wherein the transmission antenna array is independent in rotation and translation to the reception antenna array,
wherein each of the transmission antenna array and the reception antenna array is configured to rotate and translate independently.

16. The system according to claim 15,
wherein the shell comprises a solid dielectric material,
wherein the first support and the second support each comprise a material of dielectric permittivity identical to the shell.

17. The system according to claim 1, wherein the antennas of transmission and the antennas of reception are inserted into the supports.

* * * * *